US00PP31419P3

(12) United States Plant Patent
van Langen

(10) Patent No.: US PP31,419 P3
(45) Date of Patent: Jan. 28, 2020

(54) ***HAWORTHIA X ALOE* HYBRID PLANT NAMED 'AMIHAW1613'**

(50) Latin Name: ***Haworthia limifolia* x *Aloe vera***
Varietal Denomination: AMIHAW1613

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/932,611

(22) Filed: Mar. 23, 2018

(65) Prior Publication Data

US 2019/0297765 P1 Sep. 26, 2019

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

(56) References Cited

PUBLICATIONS

Plant Breeder's Right QZ PBR 20163290, Gerard van Langen, published Feb. 6, 2017.*

* cited by examiner

*Primary Examiner* — Anne Marie Grunberg
(74) *Attorney, Agent, or Firm* — Samuel R. McCoy, Jr.

(57) ABSTRACT

A new and distinct *Haworthia limifolia* x *Aloe vera* hybrid plant named 'AMIHAW1613', which is characterized by spirally-arranged succulent foliage which exhibits a star shape when viewed from above, long ovate foliage with small teeth along the length of the margins, and light greyed-green foliage with lighter greyed-green orbicular protuberances arranged in irregular transverse rows across the upper and lower leaf surfaces. The new variety has shown to be uniform and stable in the resulting generations from asexual propagation.

4 Drawing Sheets

Latin name of the genus and species: The Latin name of the genus and species of the novel variety disclosed herein is *Haworthia limifolia* x *Aloe vera*.

Variety denomination: The inventive variety of *Haworthia* x *Aloe* hybrid disclosed herein has been given the variety denomination 'AMIHAW1613'.

BACKGROUND OF THE INVENTION

Parentage: 'AMIHAW1613' is an intergeneric hybrid seedling selection resulting from the controlled pollination of an unnamed *Haworthia limifolia* plant (not patented), the seed parent, with an unnamed *Aloe vera* plant (not patented), the pollen parent. The crossing was made by the inventor in the spring of 2014 at a commercial greenhouse in Heerhugowaard, the Netherlands. In the summer of 2015, one seedling was observed which exhibited unique growth and foliage characteristics. After confirming the stability of the unique characteristics first observed, the new plant was selected for commercialization and given the name, 'AMIHAW1613'.

Asexual Reproduction: Asexual reproduction of the new cultivar 'AMIHAW1613', by way of rooting leaf cuttings, was first initiated in the summer of 2016 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIHAW1613' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIHAW1613'. These characteristics in combination distinguish 'AMIHAW1613' as a new and distinct *Haworthia* x *Aloe* hybrid cultivar:

1. 'AMIHAW1613' exhibits spirally-arranged succulent foliage in a basal rosette which exhibits a star shape when viewed from above; and
2. 'AMIHAW1613' exhibits long ovate foliage with an apiculate apex; and
3. 'AMIHAW1613' exhibits foliage with small teeth along the length of the margins; and
4. 'AMIHAW1613' exhibits light greyed-green foliage with lighter greyed-green orbicular protuberances arranged in irregular transverse rows across the upper and lower leaf surfaces; and
5. 'AMIHAW1613' exhibits spiny protuberances along the midrib of the lower leaf, particularly towards the apex.

BOTANICAL DESCRIPTION OF THE PLANT

Figure 1:
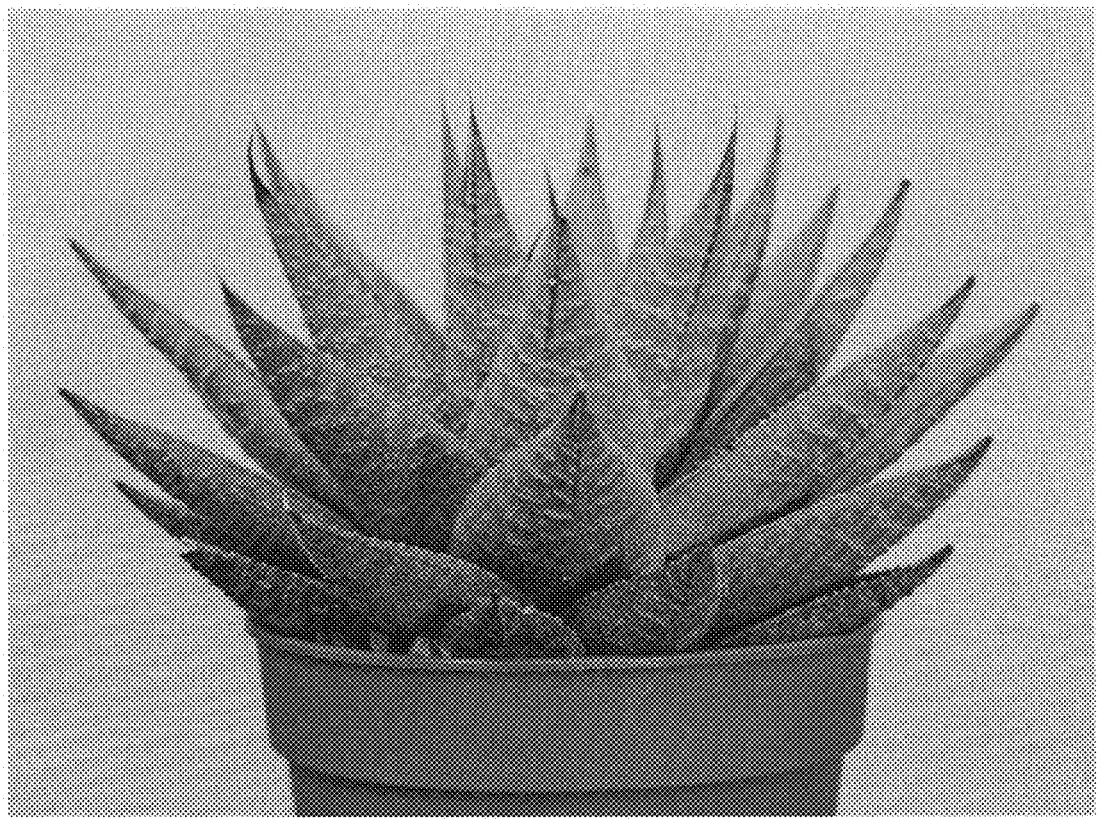
FIG. 1 illustrates, as nearly true as it is reasonably possible to make the same in color photographs of this type, an exemplary plant of 'AMIHAW1613' grown in a commercial greenhouse in Heerhugowaard, the Netherlands. This plant is approximately 12 months old, shown planted in a 12 cm container.
Figure 2:
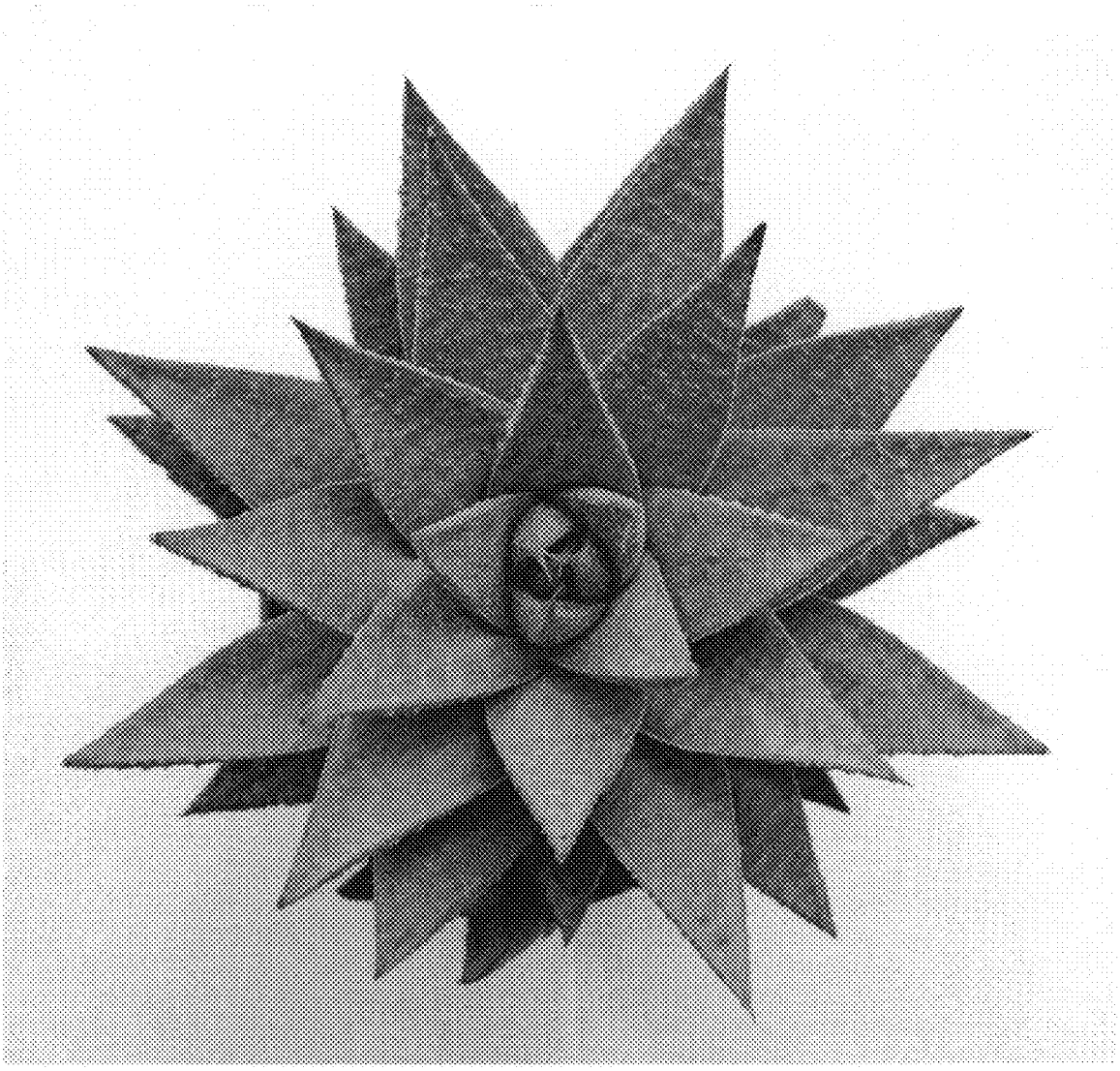
FIG. 2 illustrates, as nearly true as it is reasonably possible to make the same in color photographs of this type, the typical foliage arrangement of 'AMIHAW1613.
Figure 3:
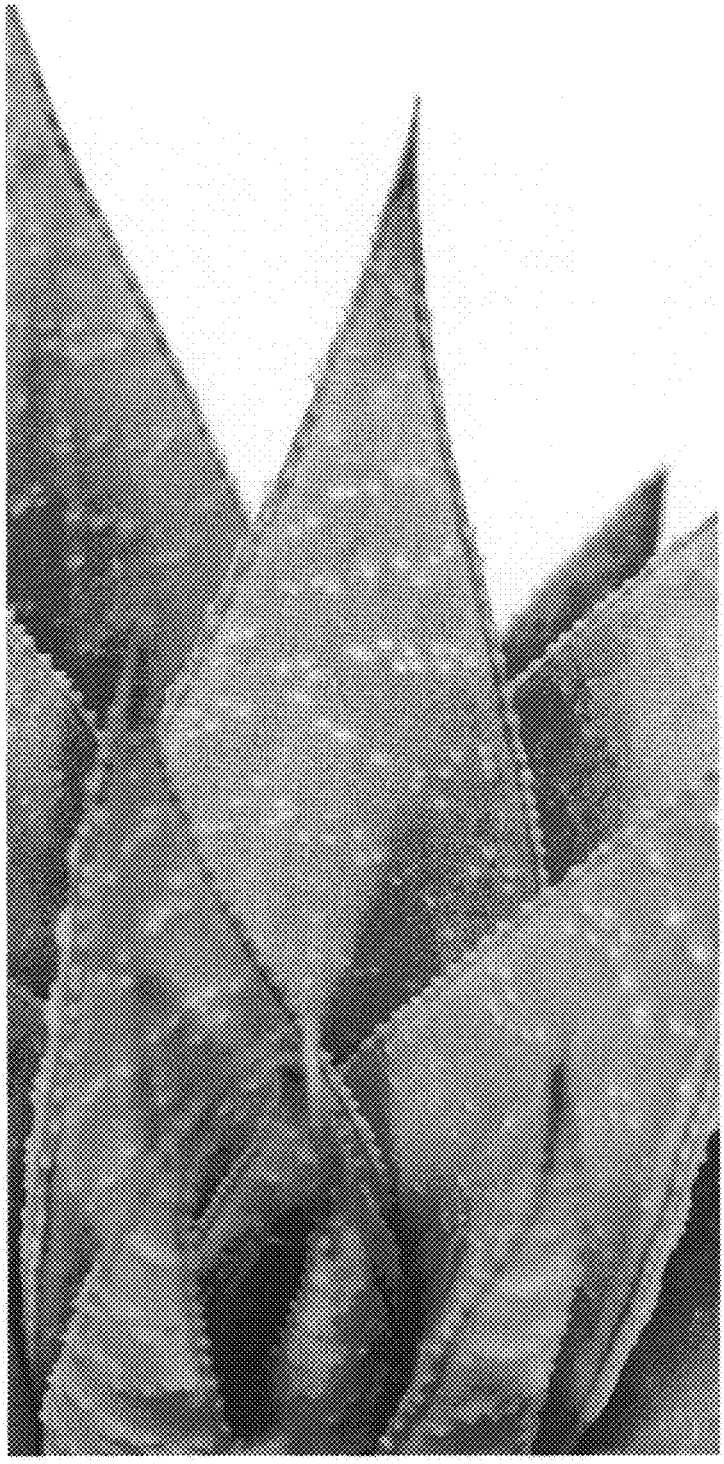
FIG. 3 illustrates, as nearly true as it is reasonably possible to make the same in color photographs of this type, the adaxial surface of the mature foliage 'AMIHAW1613'.
Figure 4:
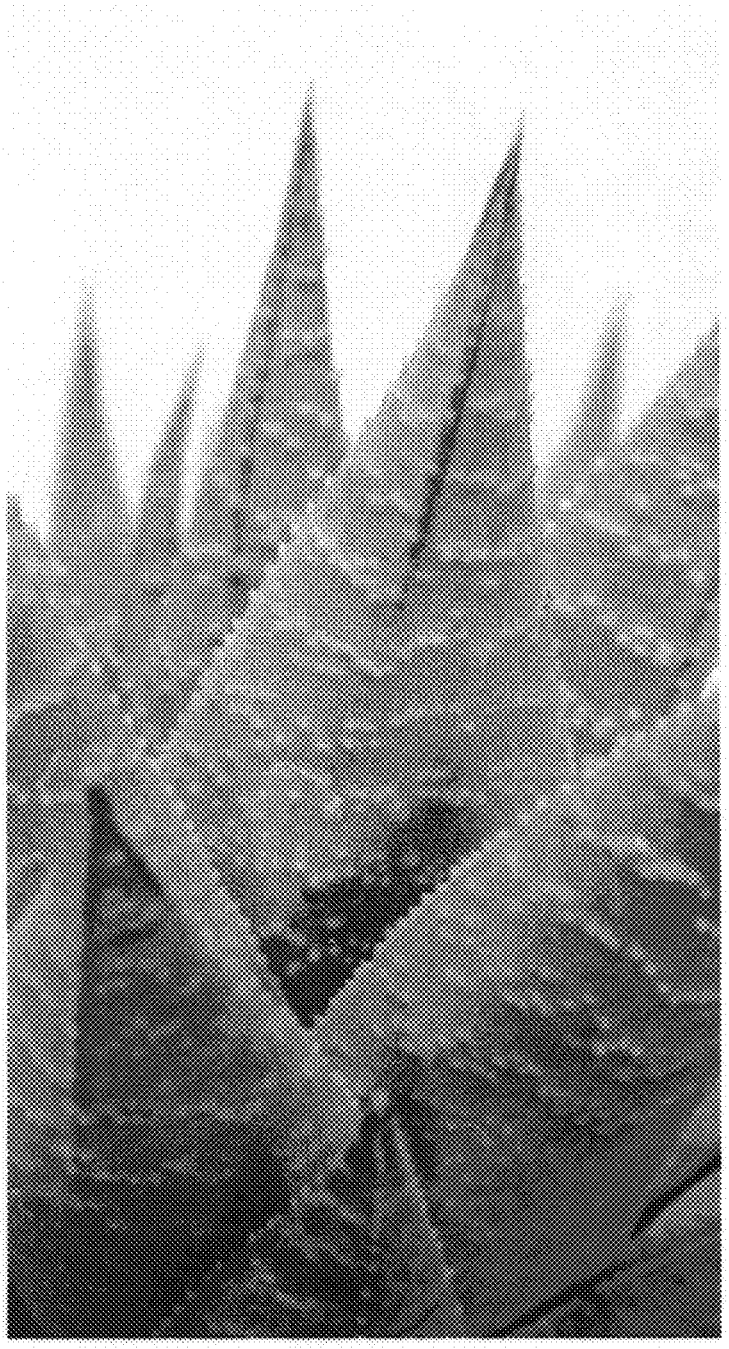
FIG. 4 illustrates, as nearly true as it is reasonably possible to make the same in color photographs of this type, the abaxial surface of the mature foliage 'AMIHAW1613'.

The following observations and measurements made in January of 2017 describe averages from a sample set of six specimens of 12 months old 'AMIHAW1613' plants grown in 12 cm nursery containers at commercial greenhouse in Heerhugowaard, the Netherlands. Plants were produced using conventional greenhouse production protocols for *Aloe* and *Haworthia* plants which consisted of minimal subsurface irrigation and minimal fertilizer applications, and chemical pest and disease control measures against mealy bug, Botrytis as required. Plants were grown under approximately 50 percent shade and no photoperiodic treatments or artificial light was given to the plants.

Those skilled in the art will appreciate that certain characteristics will vary with older or, conversely, with younger plants. 'AMIHAW1613' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIHAW1613' and a comparison with the parents and closest known comparator is provided below.

Plant description:

*Growth habit.*—Succulent perennial with foliage growing in a non-branched basal rosette.

*Plant shape.*—Flattened globular; star-shaped when viewed from above.

*Height from soil level to top of foliar plane.*—11.0 cm.

*Plant spread.*—Average of 18.0 cm.

*Growth rate.*—Moderate.

*Plant vigor.*—Moderate.

*Propagation.*—Type — Leaf cuttings. Time to initiate rooting — Approximately 28 to 35 days at 18 degrees Celsius. Crop time — Approximately 25 to 30 weeks to produce a marketable plant in a 12 cm container. Disease and pest resistance or susceptibility — Neither resistance nor susceptibility to typical *Aloe* and *Haworthia* pests and diseases has been observed. Environmental tolerances — Adapt to, at least, USDA Zones 10 to 12 and temperatures as high as 40 degrees Celsius; low tolerance to rain; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Spirally arranged in a rosette.

*Division.*—Simple.

*Attachment.*—Sessile.

*Quantity.*—39 leaves per rosette.

*Shape.*—Ovate succulent foliage.

*Dimensions.*—9.2 cm long, 3.7 cm wide, and 1.2 cm thick, on average.

*Aspect.*—Very slightly concaved and very slightly curled upward.

*Attitude.*—Upward to slightly outward.

*Apex.*—Apiculate, with a soft mucronate tip.

*Base.*—Broad cuneate.

*Margin.*—Finely dentate; teeth have an average length of 0.075 cm and are colored green-white, nearest to RHS 157D. Margins are not undulated or lobed.

*Texture, adaxial surface.*—Glabrous and moderately covered with orbicular protuberances arranged in irregular transverse rows across the leaf surface; protuberances are approximately 3.0 mm high and 1.0 mm in diameter.

*Texture, abaxial surface.*—Glabrous and densely covered with orbicular protuberances arranged in irregular transverse rows across the leaf surface; protuberances grown into soft, short spines towards the apex, approximately 5.0 mm high and 1.0 mm in diameter.

*Luster, adaxial surface.*—Matte.

*Luster, abaxial surface.*—Matte.

*Color.*—Juvenile foliage, adaxial surface — Greyed-green, nearest to RHS 191A; fading lighter towards the base, nearest to RHS 193A; darker towards the apex, nearest to RHS 189A; protuberances are colored greyed-green, nearest to RHS 192C. Juvenile foliage, abaxial surface — Greyed-green, nearest to RHS 191B; fading lighter towards the base, nearest to RHS 193A; darker towards the apex, nearest to RHS 189A; protuberances are colored greyed-green, nearest to RHS 192C. Mature foliage, adaxial surface — Greyed-green, nearest to a mixture of RHS 189A and 191B; fading lighter towards the base, nearest to RHS 194B; protuberances are colored greyed-green, nearest to a mixture of RHS 192B and 192C. Mature foliage, abaxial surface — Greyed-green, nearest to a mixture of RHS 190A and 191B; fading lighter towards the base, nearest to RHS 192A; slightly darker towards the apex, nearest to RHS 191A; protuberances are colored greyed-green, nearest to a mixture of RHS 192B and 192C.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIHAW1613' differ from the seed parent, an unnamed *Haworthia limifolia* (not patented), in the following characteristics described in Table 1 below.

TABLE 1

| Characteristic | 'AMIHAW1613' | *Haworthia limifolia* seed parent |
|---|---|---|
| Foliage length. | Longer than the parent. | Shorter than 'AMIHAW1613'. |

TABLE 1-continued

| Characteristic | 'AMIHAW1613' | *Haworthia limifolia* seed parent |
|---|---|---|
| Foliage attitude. | Upward to slightly outward. | Relaxed to somewhat upright. |
| General coloration of the mature foliage. | Light greyed-green. | Dark green. |
| Leaf protuberances. | Orbicular protuberances arranged in irregular transverse rows. | Conspicuous transverse linear protuberances presenting as raised ribs across the leaf surface. |

Plants of the new cultivar 'AMIHAW1613' differ from the pollen parent, an unnamed *Aloe vera* plant (not patented), in the following characteristics described in Table 2 below.

TABLE 2

| Characteristic | 'AMIHAW1613' | *Aloe vera* pollen parent |
|---|---|---|
| General coloration of the mature foliage. | Light greyed-green. | Dark green. |
| Leaf length. | Shorter than the parent. | Longer than 'AMIHAW1613'. |
| Leaf strength. | Stronger than parent. | Weaker than 'AMIHAW1613'. |

COMPARISONS WITH THE CLOSEST KNOWN COMPARATOR

Plants of the new cultivar 'AMIHAW1613' differ from the closest known commercial comparator, *Aloe* hybrid 'AMAIL1601' (U.S. Plant patent application Ser. No. 15/932,615), in the following characteristics described in Table 3 below.

TABLE 3

| Characteristic | 'AMIHAW1613' | 'AMIAL1601' |
|---|---|---|
| Abundance of foliage. | More abundant than 'AMIAL1601'. | Less abundant than 'AMIAL1613'. |
| General coloration of the mature foliage. | Light greyed-green. | Green. |
| Foliage aspect. | Concave and curled upward. | Concave and curled downward. |
| Foliage thickness. | Thicker than 'AMIAL1601'. | Thinner than 'AMIAL1613'. |
| Leaf protuberances. | Orbicular protuberances arranged in irregular transverse rows. | Orbicular protuberances arranged in irregular, wavy transverse rows. |

That which is claimed is:

1. A new and distinct variety of *Haworthia* x *Aloe* hybrid plant named 'AMIHAW1613', substantially as described and illustrated herein.

* * * * *